United States Patent [19]

Mitsuhashi et al.

[11] Patent Number: 5,430,171
[45] Date of Patent: Jul. 4, 1995

[54] T-BUTYL (R)-(-)-4-CYANO-3-HYDROXYBUTYRATE AND PROCESS FOR PREPARING THE SAME

[75] Inventors: Shigeru Mitsuhashi; Kazutoshi Sakurai; Hidenori Kumobayashi, all of Tokyo, Japan

[73] Assignee: Takasago International Corporation, Tokyo, Japan

[21] Appl. No.: 272,623

[22] Filed: Jul. 11, 1994

Related U.S. Application Data

[63] Continuation of Ser. No. 63,425, May 19, 1993, abandoned.

[30] Foreign Application Priority Data

Jun. 2, 1992 [JP]  Japan ................. 4-165496

[51] Int. Cl.$^6$ ........................... C07C 255/12
[52] U.S. Cl. ........................ 558/441; 558/342
[58] Field of Search ................. 558/441, 342

[56] References Cited

U.S. PATENT DOCUMENTS

| | | | |
|---|---|---|---|
| 3,427,322 | 2/1969 | Argabright et al. | 558/342 X |
| 4,611,067 | 9/1986 | Volante et al. | 549/292 |
| 4,611,068 | 9/1986 | Guindon et al. | 549/292 |
| 4,855,481 | 4/1988 | Guindon et al. | 549/292 X |
| 4,895,979 | 1/1990 | Noyori et al. | 562/567 |
| 4,994,597 | 2/1991 | Inoue et al. | 558/342 |
| 5,155,251 | 10/1992 | Butler et al. | 558/342 X |

FOREIGN PATENT DOCUMENTS

| | | |
|---|---|---|
| 0024348 | 3/1981 | European Pat. Off. . |
| 0330172 | 8/1989 | European Pat. Off. . |
| 61-146191 | 6/1986 | Japan . |
| 5-25113 | 5/1993 | Japan . |

OTHER PUBLICATIONS

Acta Chemica Scandinavica, B 37 (1983), "Synthesis of S-and R-4-Amino-3-hydroxybutyric Acid (GABOB) and S-and R-Carnitine from Arabinose or Ascorbic Acid", pp. 341-344; Bock, et. al.

Carbohydrate Research, 72 (1979), "Oxidation of L-ascorbic acid by hydrogen peroxide: preparation of L-threonic acid*", pp. 301-304; Isbell, et. al.

Bull. Chem. Soc. Fr., 33 (1923) pp. 725-733; Lespieau.

J. Med. Chem., 30 (1987), "Total Synthesis and Biological Evaluation of Structural Analogues of Compaction and Dihydromevinolin", pp. 1858-1873; Heathcock, et. al.

J. Org. Chem., 51 (1986), "Synthesis and X-ray Characterization of 6(S)-epi-Mevinolin, a Lactone Epimer", pp. 4931-4934; Stokker, et. al.

Tetrahedron Letters, 33, 17 (1992), "The Synthesis of (4R-cis)-1, 1-Dimethylethyl 6-cyanomethyl-2, 2-dimethyl-1, 3-dioxane-4—acetate", a Key Intermediate for the Preparation of CI-981,..., pp. 2279-2282; Brower, et. al.

Noller, "Chemistry of Organic Compounds", 1965, p. 274; W. B. Saunders Co., Phila. & London.

*Primary Examiner*—Joseph P. Brust
*Attorney, Agent, or Firm*—Sughrue, Mion, Zinn, Macpeak & Seas

[57] ABSTRACT

T-Butyl (R)-(-)-4-cyano-3-hydroxybutyrate having an optical purity of 99%ee or higher and a process for producing the same are disclosed, the process comprising cyanogenation of a t-butyl (S)-(-)-4-halogeno-3-hydroxybutyrate obtained by enantioselective hydrogenation of a t-butyl 4-halogenoacetoacetate. Recrystallization of the resulting crude product gives the optically active compound with high optical purity.

4 Claims, No Drawings

T-BUTYL (R)-(-)-4-CYANO-3-HYDROXYBUTYRATE AND PROCESS FOR PREPARING THE SAME

This is a continuation of Application No. 08/063,425 filed May 19, 1993, now abandoned.

FIELD OF THE INVENTION

This invention relates to t-butyl (R)-(-)-4-cyano-3hydroxybutyrate useful as an intermediate of a variety of medicines. For example, this compound is led to 4-hydroxy-3,4,5,6-tetrahydro-2H-pyran-2-one, a lactone moiety which seems to be an active site of 3-hydroxy-3-methylglutaryl coenzyme A (hereinafter abbreviated as HMG-CoA) reductase inhibitors.

BACKGROUND OF THE INVENTION (R)-(-)-4-Cyano-3-hydroxybutyric acid esters are known to be easily converted to the active lactone site of Compactin, Mevalotin and Pravastatin which are attracting attention as a cholesterol depressant or an HMG-CoA reductase inhibitor. For example, it is reported that an (R)-4-cyano-3-hydroxybutyric acid ester with its hydroxyl group protected with a trialkylsilyl group, a tetrahydropyranyl group, etc. is hydrolyzed to form an amide which is then treated with an acid to obtain (R)-4-hydroxy-3,4,5,6-tetrahydro-2H-pyran-2-one, as disclosed in U.S. Pat. No. 4,611,067.

It is also reported that an HMG-CoA reductase-inhibitor containing a phosphorus atom in the molecule thereof is obtained by halogen exchange- of methyl (S)-4-bromo-3-hydroxybutyrate prepared from iso-ascorbic acid with its hydroxyl group protected to obtain a corresponding iodide compound, which is then converted to a Wittig-Hornor reagent, followed by several additional steps, as disclosed in *J. Med. Chem.*, Vol. 33, p. 2952 (1990).

EP 0 330 172 A discloses that a 4-cyano-3-hydroxybutyric acid derivative with its hydroxyl group protected is reacted with a malonic acid derivative to obtain a 6-cyano-3-oxohexanoic acid derivative, which is further led to a cholesterol biosynthesis inhibitor.

Known processes for synthesizing optically active 4-cyano-3-hydroxybutyric esters include a pro ·ss comprising leading arabinose or ascorbic acid as a asymmetric source to methyl (S)-4-bromo-3-hydrox_ ·utyrate according to the technique described in *Acta C. ·m. Scand.*, Vol. B37, p. 341 (1983) and, after protecting the hydroxyl group with a tetrahydropyranyl group, a trialkylsilyl group, an alkyl group, etc., reacting the protected compound with sodium cyanide according to the technique as disclosed in U.S. Pat. No. 4,611,067 and a process comprising reacting L-ascorbic acid with hydrogen peroxide and calcium carbonate to form calcium L-threonate monohydrate and reacting the compound with hydrogen bromide to obtain a dibrominated compound, which is then led to a bromohydrin compound according to the process disclosed in *Carbohydrate Res.*, Vol. 72, p. 301 (1979), followed by the above-mentioned protection of the hydroxyl group and reaction with sodium cyanide.

Preparation of ethyl 4-cyano-3-hydroxybutyrate is reported in *Bull. Soc. Chim. Fr.*, (4) 33 (1923), 732, which comprises hydrolyzing 4-chloro-3-hydroxybutyronitrile to obtain a carboxylic acid, converting the carboxylic acid into its ethyl ester, and reacting the ethyl ester with potassium cyanide. However, the yield reported is low, and the literature makes no mention of optical activity.

The activity of the HMG-CoA reductase inhibitors is known to owe much to the steric configuration(s) of the hydroxyl group of the lactone moiety or of the two hydroxyl groups of the precursor β, δ-dihydroxycarboxylic acid.

For example, reduction in inhibitory activity depending on the steric configuration of the hydroxyl group is mentioned e.g., in *J. Med. Chem.*, Vol. 30, p. 1858 (1987) and *J. Org. Chem.*, vol. 51, p. 4931 (1986). That is, it is required to have high activity that the Steric configuration of the hydroxyl groups at the β- and δ-positions of β,δ-dihydroxycarboxylic acid forms a cis-configuration.

EP 0 024 348 A and U.S. Pat. Nos. 4,611,068 and 4,855,481 describe that the 4-hydroxyl group of the lactone ring of Compactin or Mevinolin must have an (R)-configuration to manifest the inhibitory activity and that conventional synthesis not only involves separation of the desired optically active compound which is accompanied with formation of an undesired isomer but also requires a very long reaction route.

In view of these reports made to date, the conventional processes have required protection of a hydroxyl group or separation of an optically active compound and involved many steps for obtaining a lactone ring moiety having high inhibitory activity. It has therefore been demanded to develop an economical synthetic process which consists of a short reaction route and is easy to carry out.

SUMMARY OF THE INVENTION

As a result of extensive investigations, the present inventors have found that t-butyl (R)-(-)-4-cyano-3-hydroxybutyrate useful as an intermediate of medicines can be obtained with ease by cyanogenation of a t-butyl (S)-(-)-4-halogeno-3-hydroxybutyrate which is easily obtained by enantioselective hydrogenation of a t-butyl 4-halogenoacetoacetate obtainable from diketene. The present invention has been completed based on this finding.

The present invention relates to t-butyl (R)-(-)-4-cyano-3-hydroxybutyrate represented by formula (I):

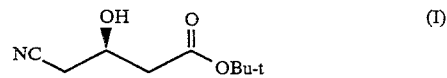

wherein Bu-t represents a t-butyl group.

The present invention also relates to a process for preparing t-butyl (R)-(-)-4-cyano-3-hydroxybutyrate represented by formula (I):

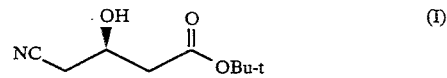

wherein Bu-t is as defined above, comprising reacting a t-butyl (S)-(-)-4-halogeno-3-hydroxybutyrate represented by formula (II):

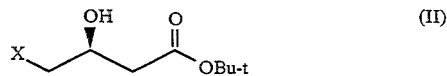

wherein Bu-t is as defined above; and X represents a chlorine atom or a bromine atom, with a cyanide represented by formula (III):

$$MCN \qquad (III)$$

wherein M represents a sodium atom or a potassium atom.

DETAILED DESCRIPTION OF THE INVENTION

The starting compound, a t-butyl 4-halogenoacetoacetate, is easily obtainable from diketene according to known processes disclosed, e.g., in JP-A-61-146191 (the term "JP-A" as used herein means an "unexamined published Japanese patent application").

The optically active compound, a t-butyl (S)-(-)-4-halogeno-3-hydroxybutyrate, can be obtained by enantioselective hydrogenation of a t-butyl 4-halogenoacetoacetate in the presence of a ruthenium-optically active phosphine complex, e.g., $Ru_2Cl_4(BINAP)_2(C_2H_5)_3N$ (wherein BINAP represents 2,2'-bis(diphenylphosphino)-1,1'-binaphthyl), according to the process described in U.S. Pat. No. 4,895,979. In this reaction, use of (R)-(+)-BINAP as a ligand of the ruthenium-optically active phosphine complex gives a desired (S)-compound. The optically active t-butyl (S)-(-)-4-halogeno-3-hydroxybutyrate may also be obtained from microorganism fermentation of a t-butyl 4-halogenoacetoacetate as described in JP-A-61-146191.

The cyanogenation can be carried out by dissolving a t-butyl (S)-(-)-4-halogeno-3-hydroxybutyrate of formula (II) in an aprotic polar solvent, such as dimethylformamide, acetonitrile or dimethyl sulfoxide, adding an aqueous solution of a cyanide of formula (III) thereto, and stirring the mixture at a temperature ranging from 15 to 100° C., and preferably from 40 to 70° C., for a period ranging from 2 to 5 hours, and preferably from 2 to 3 hours. The resulting reaction mixture is extracted with an organic solvent, e.g., ethyl acetate, toluene, diisopropyl ether or methylene chloride, the extract is washed with water, the solvent is removed by distillation, and the residue is recrystallized from toluene, ethyl acetate, ethyl alcohol, isopropyl alcohol, etc. to afford a compound of formula (I).

One of the advantages provided by the present invention is a high optical purity of the compound of formula (I). While there is no easy means available for increasing the optical purity of other lower alkyl esters (e.g., the ethyl, propyl or n-butyl ester) due to their liquid character, the compound of formula (I), being a crystal, can be obtained with an increased optical purity by recrystallization which cannot be applied to the other esters. This fact has been acquired by the present inventors for the first time.

Another advantage of the present invention resides in that the compound of formula (I) is less susceptible to saponification during cyanogenation than the other esters and therefore suffers from no great reduction in yield as encountered with the other esters.

The present invention will now be illustrated in greater detail with reference to Examples in view of Comparative Examples, but it should be understood that the present invention is not construed as being limited thereto. All the percents are by weight, except where specified. Analyses of the compounds prepared were made with instruments described below.

$^1$H-NMR: AMX-400 (400 MHz) (manufactured by Bruker, Inc.)
Internal standard: tetramethylsilane Optical Rotation: DIP-360 (manufactured by JASCO Inc.) Optical Purity and Chemical Purity:
High performance liquid chromatograph L-6000 (manufactured by Hitachi, Ltd) Detector: UV detector L-4000 UV (manufactured by Hitachi, Ltd.) IR Spectrum: IR-810 (manufactured by JASCO Inc.) Melting Point: Micro melting point apparatus (manufactured by Yanagimoto Seisakusho K.K.)

The optical purity was obtained in terms of enantiomer excess (e.e.), which, in cases where a concentration of an (R)-compound [R]is greater than that of an (S)-compound [S], is calculated according to equation:

$$\%ee = \{([R]-[S])/([R]+[S])\} \times 100$$

EXAMPLE 1

1) Preparation of t-Butyl (S)-(-)-4-Chloro-S-hydroxybutyrate:

In a 100 ml Hastelloy-made autoclave having been purged with nitrogen were charged 58.35 g (0.3 mol) of t-butyl 4-chloroacetoacetate and 120 ml of t-butyl alcohol, and solution of 250 mg (0,00015 mol) of $Ru_2Cl_4[(R)-(+)-BINAP]_2Et_3N$ in 2 ml of methylene chloride was added thereto. The mixture was stirred at 100° C. under a hydrogen pressure of 10 to 15 kg/cm² for 2 hours to conduct hydrogenation, The solvent was evaporated, and the residue was distilled under reduced pressure to give 53.0 g (percent yield: 90%) of t-butyl (S)-(-)-4-chloro-3-hydroxybutyrate as a colorless clear liquid.

The absolute configuration was determined by comparing a known product.
Optical purity: 92%ee
Boiling Point: 113°–116° C./2 mmHg
$[\alpha]^{25}_D = -94.7°$ (c=1.88, methanol)
IR (neat)$V_{max}(cm^{-1})$: 3450, 2950, 1730, 1630
$^1$H-NMRδ(ppm): 1.47 (9H, s), 2.55 (4H, m), 3.42 (1H, br s), 3.58 (2H, m), 4.22 (1H, m)

2) Preparation of t-Butyl (R)-(-)-4-Cyano-3-hydroxybutyrate:

In 120 ml of dimethyl sulfoxide was dissolved 36.7 g (0.22 mol) of the compound obtained in (1) above, and 45 ml of an aqueous solution containing 12.7 g (0.25 mol) of sodium cyanide was added thereto, followed by stirring at 65° C. for hours to give a conversion of 100%. The reaction mixture was extracted with 120 ml of ethyl acetate. The organic layer was washed with water and dried over anhydrous magnesium sulfate. The solvent was evaporated, and the residue was distilled to give 22.6 g (percent yield: 65%) of crude t-butyl (R)-(-)-4-cyano-3-hydroxybutyrate.
Optical Purity: 92%ee
Boiling Point: 130°–135° C./0.2 mmHg
Recrystallization of the crude product from 80 ml of toluene afforded 15.8 g of - t-butyl (R)-(-)-4-cyano-3-hydroxybutyrate in a percent yield of 70% based on the crude product.
Optical Purity: 99%ee or more
Melting Point: 63°–64° C.
$[\alpha]^{25}_D = -2.09°$ (c=1.05, methanol)
IR (KBr)$V_{max}$ (cm$^{-1}$): 3450, 2950, 2260, 1730, 1630, 1190
$^1$H-NMR (CDCl$_3$)δ(ppm): 1.46 (9H, s), 2.55 (2H, m), 3.45 (1H, br s), 3.59 (2H, dd, J=1.2, 5.6Hz), 4.21 (1H, m)

COMPARATIVE EXAMPLE 1

Preparation of n-Butyl (R)-(-)-4-Cyano-3-hydroxybutyrate

In a 100 ml Hastelloy-made autoclave having been purged with nitrogen were charged 38.8 g (0.2 mol) of n-butyl 4-chloroacetoacetate and 50 ml of n-butyl alcohol, and solution of 73 mg of Ru$_2$Cl$_2$[(R)-(+)-BINAP]-$_2$Et$_3$N in 2 ml of methylene chloride was added thereto. The mixture was stirred at 100° C. under a hydrogen pressure of 11 to 12 kg/cm$^2$ for 2 hours to conduct hydrogenation. The solvent was evaporated, and the residue was distilled under reduced pressure to give 35.0 g (percent yield: 90%) of n-butyl (S)-(-)-4-chloro-3-hydroxybutyrate.

Optical purity: 94%ee
Boiling Point: 118°-120° C./2 mmHg
$[\alpha]^{25}_D = -14.1°$ (c=1, chloroform)
IR (neat)V$_{max}$ (cm$^{-1}$): 3450, 2950, 1730, 1630
$^1$H-NMRδ(ppm): 0.94 (3H, t, J=7.3Hz), 1.39 (2H, m), 1.62 (2H, m), 2.63 (4H, m), 4.14 (2H, t, J=6.7Hz), 4.35 (1H, m)

The resulting compound was cyanogenated in the same manner as in Example 1-(2). That is, 58.5 g (0.3 mol) of n-butyl (S)-(-)-4-chloro-3-hydroxybutyrate was dissolved in 180 ml of dimethyl sulfoxide, and 67.5 ml of an aqueous solution containing 16.7 g (0.34 mol) of sodium cyanide was added thereto, followed by stirring at 65° C. for 2 hours. The reaction mixture was worked up in the same manner as in Example 1-(2) to obtain n-butyl (R)-(-)-4-cyano-3-hydroxybutyrate in a percent yield of 58%.

Optical Purity: 94%ee
Boiling Point: 125° C./0.5 mmHg
$[\alpha]^{25}_D = -23.5°$ (c=1.48, chloroform)
IR (neat)V$_{max}$ (cm$^{-1}$): 3450, 2950, 2260, 1730, 1630, 1190
$^1$H-NMR (CDCl$_3$)δ(ppm): 0.94 (3H, t, J=7.33Hz), 1.39 (2H, m), 1.62 (2H, m), 2.63 (4H, m), 4.14 (2H, t, J=6.7Hz), 4.35 (1H, m)

COMPARATIVE EXAMPLE 2

Preparation of Ethyl (R)-(-)-4-Cyano-3-hydroxybutyrate

In 120 ml of dimethyl sulfoxide was dissolved 36.7 g (0.22 mol) of ethyl (S)-(-)-4-chloro-3-hydroxybutyrate which had been obtained in the same-manner as in Example 1 and Comparative Example 1, and 45 ml of an aqueous solution containing 12.7 g (0.25 mol) of sodium cyanide was added thereto. The mixture was stirred at 65° C. for 2 hours to complete the reaction. The conversion attained was 90%.

The reaction mixture was extracted with 120 ml of ethyl acetate, and the organic layer was washed with 400 ml of water and dried over anhydrous magnesium sulfate. The aqueous layer was extracted twice with 60 ml portions of ethyl acetate. The combined organic layers were dried, the solvent was removed by distillation, and the residue was distilled to furnish 20 g (percent yield: 57.5%) of ethyl (R)-(-)-4-cyano-3-hydroxybutyrate.

Optical Purity: 95.6%ee
Boiling Point: 115° C./2 mmHg
$[\alpha]^{20}_D = -27.0°$ (c=1.1, chloroform)
IR (neat)V$_{max}$ (cm$^{-1}$): 3450, 2970, 2260, 1730, 1630
$^1$H-NMR (CDCl$_3$)δ(ppm): 1.29 (3H, t, J=7.2Hz), 2.63 (4H, br s), 3.42 (1H, br s), 4.20 (2H, q, J=7.2Hz), 4.34 (1H, m)

COMPARATIVE EXAMPLE 3

Preparation of Propyl (R)-(-)-4-Cyano-3-hydroxbutyrate

In the same manner as in Comparative Example 2, propyl (R)-(-)-4-cyano-3-hydroxybutyrate was obtained from propyl (S)-(-)-4-chloro-3-hydroxybutyrate in a percent yield of 56.5% with an optical purity of 95%ee.

Boiling Point: 110° C./0.3 mmHg
$[\alpha]^{25}_D = -23.6°$ (c=1.1, chloroform)
IR (neat)V$_{max}$ (cm$^{-1}$): 3450, 2950, 2260, 1730, 1630, 1190
$^1$H-NMR (CDCl$_3$)δ(ppm): 0.96 (3H, t, J=7.2Hz), 1.68 (2H, d, d, q, J=0.2, 6.7, 7.4Hz), 2.62 (4H, m), 4.10 (2H, t, J=6.7Hz ), 4.34 (1H, m )

According to the present invention, t-butyl (R)-(-)-4-cyano-3-hydroxybutyrate can be obtained with high optical purity by cyanogenation of a t-butyl (S)-(-)-4-halogeno-3-hydroxybutyrate which can be obtained by enantioselective hydrogenation of a t-butyl 4-halogenoacetoacetate easily obtainable from diketene. The present invention makes it feasible to prepare optically active t-butyl 4-cyano-3-hydroxybutyrate with an economical advantage on an industrial scale.

While the invention has been described in detail and with reference to specific examples thereof, it will be apparent to one skilled in the art that various changes and modifications can be made therein without departing from the spirit and scope thereof.

What is claimed is:

1. Tert-Butyl (R)-(-)-4-cyano-3-hydroxybutyrate having an optical purity of at least about 92%ee.

2. A novel crystalline form of tert-butyl (R)- (-)-4-cyano-3-hydroxybutyrate having an optical purity of at least about 92%ee.

3. The compound of claim 1, having an optical purity of at least about 99%ee.

4. The compound of claim 2, having an optical purity of at least about 99%ee.

* * * * *